US009781921B2

(12) United States Patent
Brown et al.

(10) Patent No.: US 9,781,921 B2
(45) Date of Patent: *Oct. 10, 2017

(54) EMULSIFIABLE CONCENTRATE FORMULATION

(71) Applicant: Huntsman Corporation Australia Pty Limited, Brooklyn (AU)

(72) Inventors: Rowan Brown, Ascot Vale (AU); Marie Giansiracusa, Reservoir (AU); Andrew F Kirby, Footscray (AU); Dilek Saylik, Ascot Vale (AU)

(73) Assignee: HUNTSMAN CORPORATION AUSTRALIA Pty Limited, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/377,322

(22) PCT Filed: Feb. 25, 2013

(86) PCT No.: PCT/AU2013/000164
§ 371 (c)(1),
(2) Date: Aug. 7, 2014

(87) PCT Pub. No.: WO2013/126947
PCT Pub. Date: Sep. 6, 2013

(65) Prior Publication Data
US 2015/0335011 A1    Nov. 26, 2015

(30) Foreign Application Priority Data

Feb. 27, 2012  (AU) ................... 2012900731

(51) Int. Cl.
*A01N 25/02* (2006.01)
*A01N 25/04* (2006.01)
*A01N 25/30* (2006.01)
*A01N 33/18* (2006.01)
*A01N 33/22* (2006.01)
*A01N 37/22* (2006.01)
*A01N 39/04* (2006.01)
*A01N 41/06* (2006.01)
*A01N 43/40* (2006.01)
*A01N 43/52* (2006.01)
*A01N 43/653* (2006.01)
*A01N 47/22* (2006.01)
*A01N 47/38* (2006.01)
*A01N 47/44* (2006.01)
*A01N 51/00* (2006.01)
*A01N 53/00* (2006.01)

(52) U.S. Cl.
CPC .......... *A01N 25/02* (2013.01); *A01N 25/04* (2013.01); *A01N 25/30* (2013.01); *A01N 33/18* (2013.01); *A01N 33/22* (2013.01); *A01N 37/22* (2013.01); *A01N 39/04* (2013.01); *A01N 41/06* (2013.01); *A01N 43/40* (2013.01); *A01N 43/52* (2013.01); *A01N 43/653* (2013.01); *A01N 47/22* (2013.01); *A01N 47/38* (2013.01); *A01N 47/44* (2013.01); *A01N 51/00* (2013.01); *A01N 53/00* (2013.01)

(58) Field of Classification Search
CPC ........ A01N 25/02; A01N 25/04; A01N 25/30; A01N 33/18; A01N 33/22; A01N 37/22; A01N 39/04; A01N 41/06; A01N 43/40; A01N 43/52; A01N 43/653; A01N 47/22; A01N 47/38; A01N 47/44; A01N 51/00; A01N 53/00
See application file for complete search history.

(56) References Cited

U.S. PATENT DOCUMENTS

| 4,452,630 | A | 6/1984 | Dalmoro et al. |
| 4,940,484 | A * | 7/1990 | Hewett ................ A01N 43/40 504/130 |
| 5,444,078 | A | 8/1995 | Yu et al. |
| 5,846,997 | A | 12/1998 | Sirinyan et al. |
| 6,635,663 | B1 | 10/2003 | Zen |
| 8,097,631 | B2 | 1/2012 | Stock et al. |
| 2004/0082476 | A1 | 4/2004 | Haesslin et al. |
| 2009/0005246 | A1 | 1/2009 | Schneider |
| 2009/0137649 | A1 | 5/2009 | Pedersen |
| 2011/0045975 | A1 | 2/2011 | Ehr et al. |

FOREIGN PATENT DOCUMENTS

| JP | 2009-173569 A | 8/2009 |
| JP | 2009-173596 A | 8/2009 |
| WO | 2007/068420 A | 6/2007 |
| WO | 2008/006456 A | 1/2008 |

OTHER PUBLICATIONS

Miscibility of Organic Solvents"in: Chemische Tabellen und Rechentafeln fur die analytische Praxis", Jan. 1, 1986, VEB Deutscher Verlag fur Grundstoffindustrie, Leipzig, German Democratic Republic (GDR), XP055218391; ISBN: 978-3-342-00107-2, pp. 228-229.

* cited by examiner

*Primary Examiner* — John Pak
*Assistant Examiner* — Nathan W Schlientz
(74) *Attorney, Agent, or Firm* — Huntsman Corporation Australia Pty Limited; Edward Korompai

(57) ABSTRACT

An emulsifiable concentrate (EC) formulation comprising a least one agrochemical active ingredient; at least one surfactant emulsifier; optionally, a stabilizer; and a primary solvent system, wherein the solvent system comprises a combination of benzyl acetate and a sufficient amount of at least one polar, substantially water-miscible co-solvent.

15 Claims, No Drawings

EMULSIFIABLE CONCENTRATE FORMULATION

CROSS-REFERENCE TO RELATED APPLICATIONS

This application is the National Phase of International Application PCT/AU2013/000164 filed Feb. 25, 2013 which designated the U.S. and which claims priority to Australia Application Serial No. 2012900731 filed Feb. 27, 2012. The noted applications are incorporated herein by reference.

FIELD OF THE INVENTION

The invention relates to an emulsifiable concentrate (EC) formulation of agrochemical active ingredients utilising an improved solvent system comprising benzyl acetate as a primary solvent in combination with other co-solvents. More preferably, the improved solvent system provides a substantially storage-stable and dilution-stable emulsifiable concentrate (EC) formulation.

BACKGROUND OF THE INVENTION

In the art of formulating agrochemicals, it is often necessary to dissolve the agrochemical active ingredient in a solvent and then dilute it in a larger volume of water in order for it to be broadcast in the form of a fine spray. In still other cases, it is necessary to dilute the active ingredient in a solution and apply it to a seed or other solid carrier. While some active ingredients, which are usually in the form of a salt, can be simply dissolved and then diluted in water, the majority of agrochemical active ingredients are hydrophobic and are therefore not water-soluble. In the case of active ingredients that are not water-soluble, it is normally necessary to dissolve the formulation in a water-immiscible solvent and add one or more surfactants, so that the solution will form an oil-in-water emulsion, when added to water. Such a formulation is called an Emulsifiable Concentrate (EC) formulation. Alternatively, the water-immiscible solution comprising active ingredient can be pre-emulsified in water in a concentrated form. Such a formulation is called an Emulsion-in-Water (EW) formulation. A special sub-class of EW formulations is the so-called Microemulsion (ME) formulation, where the emulsion particle size is such that the formulation does not scatter light and has a clear or translucent appearance.

Water-immiscible solvents commonly used for EC and EW formulations include, but are not limited to, aromatic hydrocarbons such as the SOLVESSO® series, paraffinic hydrocarbons such as the EXXSOL® range, ester solvents such as the EXXATE® range, all of which are manufactured by EXXONMOBIL, and ester solvents such as methyloleate. Further, solvents which are water-immiscible at high concentration include cyclic hydrocarbons, such as cyclohexanone and isophorone.

In more recent times, solvents which exhibit improved toxicity and reduced flammability profiles have been used. These include the dibasic ester solvents of long chain di-acids having from 8-16 carbon units, which are usually methyl ester derivatives, and fatty acid amide solvents, examples of which are the dimethylamide and morpholineamide derivatives of $C_6$-$C_{16}$ fatty acids. Mono-alkylene carbonates such as ethylene, propylene and butylene carbonates, also find use as co-solvents.

Combinations of water-immiscible solvents with highly polar water-miscible co-solvents such as N-methyl pyrrolidinone, dimethylsulphoxide, dimethylisosorbide, monoethylene glycol, monopropylene glycol and various glycol ethers have been used in the past to achieve physical stability of the EC formulation, particularly if crystallisation of the active ingredient occurs at below ambient temperature. However, the use of such solvent combinations often leads to the problem of crystallisation in the diluted formulation.

There is a particular need for low toxicity and low flammability polar solvents, which can dissolve the more polar active ingredients, but which are not so polar as to have significant water-solubility problems resulting in crystallisation of the active ingredient upon dilution. In particular, it is desirable to be able to dissolve certain problematic agrochemical active ingredients in high concentration for use in emulsifiable concentrate formulations. High concentration ECs have significant advantages in terms of the reduced costs involved in shipping and handling. Such active ingredients include, but are not limited to, pyridine-based herbicides such as clopyralid and diflufenican; diphenylether herbicides such as oxyfluorfen; anilide herbicides such as propanil; triazole fungicides such as triadimenol; dinitroaniline herbicides such as oryzalin; carbamate insecticides such as propoxur; oxadiazine insecticides such as indoxacarb; synthetic pyrethroid insecticides such as bifenthrin; and neonicotinoid insecticides such as imidacloprid and thiocloprid.

While many of the dibasic ester and fatty amide-based solvents can dissolve some of the active ingredients in the polarity range of these solvents, there are limitations on the amount of active ingredient that can be dissolved. Further, not all of these classes of solvents have desirable toxicity profiles. In addition, significant effort and expense can be involved in the manufacture and, in particular, the purification of these solvents.

While mono-short chain alkylene carbonate solvents have an overall excellent toxicity profile and reduced flammability, their major limitation is that they are generally water-miscible upon dilution and do not fully dissolve many of the active ingredients described above.

The use of benzyl acetate as a solvent for agrochemical active ingredients is known. Japanese Patent Application No. JP 2009173569A teaches the use of benzyl acetate and butylacetoacetate in combination with a water-miscible co-solvent, 1,3-dimethyl-2-imidazolidinone and an aromatic hydrocarbon to prepare emulsion compositions of various hydrophobic agrochemical active ingredients up to 50 weight/volume %. International Patent Publication No. WO 2011/017480 teaches the use of benzyl acetate as a suitable solvent for dissolving certain active ingredients in preparation for forming microcapsule compositions.

There is, however, still a need for polar, water-miscible solvent combinations having an improved toxicity and flammability profile.

The present invention seeks to provide an improved solvent system for high concentration emulsifiable concentrate formulations that at least ameliorates certain disadvantages associated with previously known solvent systems.

SUMMARY OF THE INVENTION

According to one aspect of the present invention, there is provided an emulsifiable concentrate (EC) formulation comprising a least one agrochemical active ingredient; at least one surfactant emulsifier; optionally, a stabiliser; and a primary solvent system, wherein the solvent system comprises a combination of benzyl acetate and a sufficient amount of at least one polar, substantially water-miscible co-solvent.

The present inventors have now surprisingly found that when benzyl acetate is used in combination with other substantially water-miscible co-solvents described herein as the primary solvent system, storage-stable and dilution-stable formulations of certain problematic active ingredients can be achieved at higher loadings than could previously be achieved with alternative solvent combinations. Such a primary solvent system has an improved toxicity and flammability profile.

In particular, it has been found that when used with polar, substantially water-miscible co-solvents, for example, N-methyl pryrrolidinone and dimethylsulphoxide, benzyl acetate is able to afford formulations, which are both stable in concentrate form and stable to crystallisation upon dilution in water. That is, benzyl acetate is able to substantially overcome the problem of crystallization on dilution which is often associated with using polar, substantially water-miscible solvents as co-solvents to achieve the desired solubility in the concentrate.

The ratio of benzyl acetate to the water-miscible co-solvent is preferably in the mixing range of from 99.9:0.1 to 40:60 and more preferably, in the range of from 90:10 to 60:40.

The at least one substantially water-miscible co-solvent is preferably selected from the group of N-methylpyrrolidinone (NMP); dimethylsulphoxide (DMSO); dimethylformamide (DMF); dimethylisosorbide (DMI); isophorone; acetophenone; cyclohexanone; 1,3-dimethyl-2-imidazolidonone; ethylene, propylene and butylene carbonates; lactate esters; dimethyl and diethylcarbonates; alkylglycol ethers; glycols including propylene glycol, ethylene glycol and polyethylene glycols; alcohols including methanol; ethanol; iso-propanol; n-propanol; n-butanol; iso-butanol; and tert-butanol; or mixtures thereof.

The active ingredient is preferably selected from a pesticide or an herbicide, such as from pyridine-based herbicides; diphenylether herbicides; anilide herbicides; dinitroaniline herbicides; triazole fungicides; carbamate insecticides; oxadiazine insecticides; and neonicotinoid insecticides; or mixtures thereof.

More preferably, the active ingredient is selected from clopyralid, diflufenican, oxyfluorfen, propanil, triadimenol, oryzalin, propoxur, bifenthrin, indoxacarb, imidacloprid and thiacloprid, or mixtures thereof.

In a most preferred form, the active ingredient is diflufenican present at greater than 2% weight/volume. In a further preferred form, the formulation of the present invention further comprises a phenoxyacid ester herbicide.

In a preferred form, the at least one surfactant emulsifier used in the EC formulation is selected from the group comprising alkoxylated alcohols; alkoxylated alkylphenols; ethoxylated fatty acids; ethoxylated vegetable oils; ethoxylated tristyrylphenol; fatty acid esters of sorbitol and ethoxylated derivatives thereof; ethoxylated amines and condensates of glycerol; sulfonated alkylbenzenes in the range $C_{11}$-$C_{16}$ and salts thereof; alkylether sulphates; alkyletherphosphates; alkylphenoletherphosphates; or combinations thereof; salts of phosphate esters of ethoxylated tristyrylphenol; salts of sulphated ethers of ethoxylated tristyrylphenol; or a catanionic system, wherein a cationic amine is present in combination with an alkylsulphonate, an alkylethersulphonate, an ether sulphate, or an ether phosphate such as an alkyletherphosphate.

The EC formulation of the present invention preferably further comprises a stabiliser, selected from butylated hydroxytoluene (BHT) and epoxidized soybean oil (ESBO). The stabiliser is preferably present in a concentration of up to 3% weight/volume and is more preferably added to the formulation once the active ingredient is dissolved in the solvent system.

Combinations of benzyl acetate with polar, substantially water-miscible co-solvents have been found to have good utility with certain crystalline active ingredients including, but not limited to, pyridine-based herbicides such as clopyralid and diflufenican; diphenylether herbicides such as oxyfluorfen; anilide herbicides such as propanil; triazole fungicides such as triadimenol; dinitroaniline herbicides such as oryzalin; carbamate insecticides such as propoxur; oxadiazine insecticides such as indoxacarb; and neonicotinoid insecticides such as imidacloprid and thiacloprid. It was been found that these active ingredients can be formulated at a sufficiently high loading to produce stable and more commercially desirable formulations, while at the same time, maintaining an acceptable toxicity profile and low flammability.

The scope of the present invention also extends to methods of formulating agrochemical active ingredients without using either further harmful or high odour solvents. In a second aspect, the present invention is directed to a method of making an emulsifiable concentrate (EC) formulation of at least one agrochemical active ingredient comprising the following steps of either firstly forming a mixture of the agrochemical active ingredient in a polar, substantially water-miscible co-solvent and then adding benzyl acetate; or alternatively forming a mixture of the agrochemical active ingredient in benzyl acetate and then adding a polar, substantially water-miscible co-solvent; or alternatively forming a mixture of the agrochemical active ingredient in a combination of benzyl acetate and a polar, substantially water-miscible co-solvent; or alternatively combining the agrochemical active ingredient, benzyl acetate and a polar, substantially water-miscible co-solvent; followed by adding at least one suitable emulsifier/s and/or at least one stabilizer/s to make an EC formulation, whereby the active ingredient is substantially soluble at 0° C. on storage in the presence of seed crystals.

The present invention is also directed to a method of making an emulsion-in-water (EW) formulation comprising at least one agrochemical active ingredient, the method comprising the following steps of either firstly, forming a mixture of the agrochemical active ingredient in a polar, substantially water-miscible co-solvent and then adding benzyl acetate; or alternatively forming a mixture of the agrochemical active ingredient in benzyl acetate and then adding a polar, substantially water-miscible co-solvent; or alternatively forming a mixture of the agrochemical active ingredient in a combination of benzyl acetate and a polar, substantially water-miscible co-solvent; or alternatively, combining the agrochemical active ingredient, benzyl acetate and a polar, substantially water-miscible co-solvent; followed by adding at least one suitable surfactant emulsifier/s and/or at least one stabilizer/s to make an emulsifiable formulation; and then contacting the composition with water, whereby the active ingredient is substantially soluble at 0° C. on storage in the presence of seed crystals.

A further advantage in using benzyl acetate solvent is that it is relatively cheap compared to many of the specialty solvents, which may be able to achieve high loading formulations of similar strength. An additional advantage is that benzyl acetate has a low odour.

Further, it has been found that benzyl acetate together with other co-solvents can usefully be emulsified together with one or more desired active ingredients using conventional surfactants known to be useful as emulsifiers for agrochemical formulations, such as EC formulations. In other words, the benzyl acetate solvent does not require any specialized emulsifier systems to achieve a stable emulsion upon dilution.

DESCRIPTION OF THE PREFERRED EMBODIMENT

It can be seen from the physical properties of benzyl acetate, which are summarized in Table 1 below, that this solvent shows relatively low volatility and flammability.

TABLE 1

| Physical Properties of Benzyl Acetate | Result |
|---|---|
| Boiling point, ° C. | 212 |
| Melting Point, ° C. | −51 |
| Density, g/cm$^3$ | 1.04 |
| Solubility in water, % w/w | <1 |
| Viscosity @45° C., cP | 1.4 |
| Flashpoint, ° C. | 90 |
| Auto-ignition temperature, ° C. | 460 |

The toxicological properties of benzyl acetate are summarized in Table 2 as follows:

TABLE 2

| Toxicity of Benzyl Acetate | Result |
|---|---|
| Acute oral toxicity, LD50 (est) mouse, mg/kg | 830 |
| Acute dermal toxicity, LD50 (est) rabbit, mg/kg | >500 |
| TLV as TWA, ppm | 10 |

Benzyl acetate shows relatively low toxicity.

In order for a solvent to be effective for an agrochemical formulation, such as an EC or EW, it is necessary for the active ingredient to be sufficiently soluble, such that no crystallisation of it is observed in the temperature range of from 0° C. to 54° C. and more preferably, in the temperature range of from −5° C. to 54° C. A number of polar, substantially water-miscible co-solvents have been found to be useful with problematic agrochemical active ingredients in achieving stability of the formulation concentrate to crystallisation. Such solvents include, but are not limited to: N-methylpyrolidinone (NMP), dimethylsulphoxide (DMSO), dimethylformamide (DMF), dimethylisosorbide (DMI), isophorone, acetophenone and cyclohexanone and various lactate ester derivatives. A major difficulty with using these types of polar solvents is that while the problem of crystallisation can be solved, the stability of the diluted formulation and resulting emulsion is inadequate regarding crystallisation of the active ingredient.

An EC formulation is preferably diluted in water at rates ranging from 0.1 to 20% w/v and more preferably, in the range of 0.5 to 5% w/v. In order for an EC formulation to be useable, it should not show crystallisation in the diluted emulsion before spraying and it must be stable for the time allowed between dilution and spraying. Typical time standards for dilution stability of active ingredients are set out by the Food and Agriculture Organization of the United Nations (FAO) and may be found in the various technical monographs prepared by them. For emulsion stability, it is expected that a formulation upon dilution would be substantially free of crystals for more than 2 hours, and more preferably, for more than 24 hours.

Accordingly, it has been surprisingly found that if a sufficient amount of benzyl acetate is used in combination with a sufficient amount of at least one polar, substantially water-miscible co-solvent such as, for example, NMP, DMI or DMSO, as the primary solvent system, sufficient solubility to certain crystalline active ingredients is afforded to maintain stability of the emulsifiable concentrate (EC) formulation, whilst also affording stability on dilution in water regarding crystallisation.

The term "primary solvent" as used herein is a solvent or combination of solvents which must be present to dissolve the active ingredient. The term "non-primary solvent" as used herein is a solvent which may optionally also be present in the solvent system, but which is not required for the purposes of dissolving the active ingredient. A non-primary solvent may incidentally be present in emulsifier blends, or as an agent, which adds additional features or characteristics, such as colour, stability or viscosity to the overall formulation. In general, if less than about 10% of a non-primary solvent is present, such a solvent will not function as part of the primary solvent system.

The polar, substantially water-miscible co-solvents useful in the present invention preferably include, but are not limited to: N-methylpyrrolidinone (NMP); dimethylsulphoxide (DMSO); dimethylformamide (DMF); dimethylisosorbide (DMI); isophorone; acetophenone; cyclohexanone; 1,3-dimethyl-2-imidazolidonone; ethylene, propylene and butylene carbonates; dimethyl and diethylcarbonates; alkylglycol ethers; glycols such as propylene glycol, ethylene glycol and polyethylene glycols; alcohols such as methanol, ethanol, iso-propanol, n-propanol, n-butanol, iso-butanol and tert-butanol. In order to be considered substantially water-miscible, the solvent should have at least substantially, preferably, complete water-solubility at the anticipated dilution rates of the EC formulation, which are typically greater than 1 part in 1,000.

The terms "agrochemical active" or "agrochemically active" as used herein are intended to also cover all the related uses of the EC formulations, such as in animal health, public health, water treatment, wood treatment, home garden and domestic vector control. The agrochemical active ingredients useful in the present invention preferably include those as listed in The Pesticide Manual of the British Crop Protection Council (14$^{th}$ Edition), which are soluble in polar, substantially water-immiscible solvents.

The active ingredient/s and EC formulation's, wherein there is advantageous dilution performance in regard to a lack of crystallisation than would otherwise be observed in the absence of benzyl acetate, preferably include/s, but is/are not limited to, diflufenican alone or diflufenican in the presence of phenoxyacid ester herbicide, oxyfluorfen, propanil and/or imidacloprid.

Benzyl acetate is preferably used with the substantially water-miscible co-solvent in a ratio range of from 99.9:0.1 to 40:60, more preferably, in the range of from 90:10 to 60:40, as the primary solvent system.

The present invention may further comprise one or more substantially water-immiscible or partially water-immiscible co-solvent/s as a non-primary solvent, so long as such a solvent is not present in sufficient quantity to re-induce crystallisation of the active ingredient upon dilution in water or storage. Typically, the water-immiscible co-solvent is present at no more than 10% w/v in the total formulation used.

The agrochemical formulations of the present invention are preferably applied to plant leaves as foliar sprays, or to plant shoots and the surrounding soil. Such formulations may also be applied to animals, either topically, orally or as injectables. They may also be applied directly to insects, acarina, fungi, molluscs, nematodes and helminths, to wood and wood products and as a component of mixtures applied as coatings for buildings, insect protection nets and so on.

The composition of the active ingredient/s made using the primary solvent combination is preferably formulated as an emulsifiable concentrate (EC), or also as an oil-in-water emulsion (EW) made from such a concentrate. In order to make an EC formulation, other additives such as emulsifiers and stabilisers are preferably used. Such additives may add or subtract from the total solubility level of the active ingredient/s depending upon what is used. For example, surfactant emulsifiers containing a salt of dodecylbenzene sulphonate, such as the calcium salt or one or more amine salts, preferably contain additional solvents, like short chain alcohols, which enhance overall solubility. However, in other situations, the addition of emulsifiers may dilute the total level of the active ingredient in the formulation.

In order to prepare a preferred EC formulation, the active ingredient/s is/are dissolved in the benzyl acetate/substantially water-miscible co-solvent combination and surfactant emulsifiers are added in the range 3-20% w/v and the formulation made up to the required volume. Optionally, prior to making the formulation up to the required volume, further co-solvents which may be substantially water-miscible or partially water-miscible may be added. Such optional co-solvents preferably include, but are not limited to, a cyclic hydrocarbon/s such as cyclohexanone and isopherone; mono-alkylene carbonates, such as ethylene, propylene and butylene carbonates; or dibasic esters.

Emulsifiers for the EC formulations preferably include, but are not limited to, non-ionic surfactants, such as alkoxylated alcohols and alkoxylated alkylphenols; ethoxylated fatty acids; ethoxylated vegetable oils such as ethoxylated castor oil; ethoxylated tristyrylphenol; fatty acid esters of sorbitol and ethoxylated derivatives thereof; ethoxylated amines, and condensates of glycerol. Anionic surfactants such as salts of sulphonated dodecylbenzene and other alkylbenzenes in the range $C_{11}$-$C_{16}$ and salts thereof; alkylether sulphates; and ether phosphates including alkyletherphosphates; alkylphenoletherphosphates; or combinations thereof; salts of phosphate esters of ethoxylated tristyrylphenol and salts of sulphated ethers of ethoxylated tristyrylphenol, can be used as emulsifiers. Catanionic systems, where a cationic amine is present in combination with an alkylsulphonate, an alkylethersulphonate, an ether sulphate or an ether phosphate such as alkyletherphosphate, can also be useful.

The emulsifiers for EC formulations can be selected from the group of castor oil ethoxylates, in particular TERMUL® 1284 emulsifier; alkoxylated alcohols, in particular TERMUL® 5459 emulsifier; alkoxylated alkylphenols, in particular TERMUL® 200 emulsifier; ethoxylated amines, in particular TERWET® 3784 and TERIC® 16M15 emulsifiers; ethoxylated tristyrylphenol, in particular TERMUL® 3150 emulsifier; alcohol ethoxylates in particular TERIC® 12A7, 13A9 and 17A2 emulsifiers; fatty acid ethoxylates such as TERIC® OF6 emulsifier; sorbitan ester ethoxylates, such as ECOTERIC® T85 emulsifier; a sulphosuccinate, such as TERMUL® 3665 emulsifier, amine and calcium salts of dodecylbenzene sulphonate, such as the NANSA® EVM range of products; salts of phosphate esters of ethoxylated tristyrylphenol, in particular TERSPERSE® 2202; salts of sulphated ethers of ethoxylated Tristyrylphenol, in particular TERSPERSE® 2218; all of which are available from Huntsman Corporation.

The EC formulation should, upon dilution, give a stable emulsion free of crystallisation for a sufficient time period, preferably at least two hours, to allow convenient use. Such emulsion stability is usually determined visually by measuring the amount of cream or sediment which forms in a diluted solution of the active ingredient after the required time period. The tests required to determine the internationally acceptable standards for stability of EC formulations may be found in the Handbooks as provided by the Collaborative International Pesticides Analytical Council (CIPAC). A typical test method used would be CIPAC MT36.3. The internationally acceptable standard of emulsion stability, as determined by the CIPAC methods, for various active ingredients are provided by the Food and Agriculture Organization of the United Nations (FAO) and may be found in the various technical monographs prepared by them.

The use of benzyl acetate together with substantially water-miscible co-solvents in EC formulations of the present invention is demonstrated with reference to the following non-limiting Examples.

EXAMPLES

Cold Storage Stability

Example formulations were seeded with at least one crystal of the active ingredient being investigated and stored at 0° C. for 7 days as per the cold storage stability testing methodology outlined in CIPAC MT39.1 (CIPAC Volume F, p128). On completion of the 7 day storage, the formulations were assessed for visible signs of crystal growth.

Accelerated Storage Stability

Example formulations were stored at 54° C. for 14 days as per the accelerated storage stability testing methodology outlined in CIPAC MT46.1.3 (CIPAC Volume F, p150). Following 14 days storage, the formulations were assessed for stability, paying particular note to sedimentation or separation.

Emulsion Stability Test

Example formulations were evaluated according to CIPAC MT36.1.1 (CIPAC volume F, p108) at ambient temperature. The volume percent of cream and the presence or otherwise of crystals after 0.5, 1, 2, and 24 hours was observed and recorded for a 5 in 100 parts dilution. The emulsion tubes were subsequently inverted 10 times and a final reassessment was made at 24.5 hours.

The purpose of the emulsion test in this instance is to look for the development of crystals upon dilution. An effort was not made to fully optimize the emulsion performance with respect to cream and oil separation.

| 25 g/L DIFLUFENICAN | |
|---|---|
| Formulation | g/L |
| Diflufenican | 25 |
| TERMUL ® 5459 | 30 |
| NANSA ® EVM 70/2E | 30 |
| NMP | 150 |
| Solvent | to volume (1 Liter) |

Example 1

In an appropriately sized beaker, 25 g/L of diflufenican was weighed, followed by the addition of 150 g/L of NMP, 30 g/L of TERMUL® 5459 and 30 g/L of NANSA® EVM 70/2E. The formulation was then made to the required volume with benzyl acetate, and stirred over moderate heat (approx. 60° C.) for 15 minutes until homogenous.

Example 2 (Comparative Example)

In an appropriately sized beaker, 25 g/L of diflufenican was weighed, followed by the addition of 30 g/L of TERMUL® 5459 and 30 g/L of NANSA® EVM 70/2E. The formulation was then made to the required volume with benzyl acetate, and stirred over moderate heat (approx. 60° C.) for 15 minutes until homogenous.

Example 3 (Comparative Example)

As for Example 1, the formulation was made to the required volume with Solvesso® 200, and then stirred over moderate heat (approx. 60° C.) for 15 minutes until homogenous.

Example 4 (Comparative Example)

As for Example 1, the formulation was made to the required volume with Solvesso® 150, and then stirred over moderate heat (approx. 60° C.) for 15 minutes until it was homogenous.

| Storage Stability Results | | | | |
|---|---|---|---|---|
| Appearance | Example 1 | Example 2 | Example 3 | Example 4 |
| Initial | Clear, light yellow, homogenous solution | Clear, light yellow, homogenous solution | Clear, light yellow, homogenous solution | Clear, light yellow homogenous solution |
| Post-storage, (7 days at 0° C., seeded) | Clear solution, no crystals observed | Hazy solution with crystal growth observed. Crystals soluble on thawing | Hazy solution with crystal growth observed. Crystals insoluble on thawing | Hazy solution, which becomes clear at room temperature |
| Post-storage (2 weeks at 54° C.) | Clear, yellow, homogenous solution | Clear, yellow, homogenous solution | Clear, yellow, homogenous solution | Clear, yellow, homogenous solution |

| Emulsion Stability Results | | | | | | | | |
|---|---|---|---|---|---|---|---|---|
| Water Hardness (ppm) | Bloom | Ease of Dispersion in water | Volume (ml) creaming/oil with elapsed time | | | | | |
| | | | Initial | ½ hour | 1 hour | 2 hours | 24 hours | 24.5 Hours |
| Example 1 | | | | | | | | |
| 20 | Poor | Excellent | Homogenous, thick white emulsion | 1.3 ml bottom cream | 2.0 ml bottom cream | 2.8 ml bottom cream | 6.0 ml bottom cream, trace oil | 1.3 ml bottom cream |
| 342 | Poor | Excellent | Homogenous, thick white emulsion | 0.2 ml bottom cream | 0.2 ml bottom cream | 0.2 ml bottom cream | 5.4 ml bottom cream, trace oil | 0.2 ml bottom cream |
| 1026 | Poor | Excellent | Homogenous, thick white emulsion | 0.6 ml bottom cream | 1.2 ml bottom cream | 1.8 ml bottom cream | 4.7 ml bottom cream, trace oil | 0.6 ml bottom cream |
| Example 2 | | | | | | | | |
| 20 | Poor | Good | Homogenous, thick white emulsion | nil cream/oil | Nil cream/oil | Nil cream/oil | Nil cream/oil, fine crystals observed | Nil cream/oil |
| 342 | Poor | Good | Homogenous, thick white emulsion | 6.4 ml top oil layer | 6 ml top oil layer | 6.5 ml top oil layer | 6.5 ml top oil, 4 ml bottom crystallisation observed. | 6.0 ml top oil, 2 ml bottom crystals |
| 1026 | Poor | Good | Homogenous, thick white emulsion | 6 ml top oil | 6 ml top oil | 6 ml top oil | 6 ml top oil, long, fine crystals observed. | 6 ml top oil |
| Example 3 | | | | | | | | |
| 20 | Poor | Excellent | Homogenous, thick white emulsion | 0.4 ml bottom cream | 0.4 ml bottom cream | 0.5 ml bottom cream | 7.2 ml bottom cream, trace oil | 0.4 ml bottom oil |
| 342 | Poor | Excellent | Homogenous, thick white emulsion | nil cream/oil | 0.3 ml bottom cream | 0.3 ml bottom cream | 7 ml bottom cream, trace oil | Nil cream/oil |

-continued

| Water Hardness (ppm) | Bloom | Ease of Dispersion in water | Volume (ml) creaming/oil with elapsed time | | | | | |
|---|---|---|---|---|---|---|---|---|
| | | | Initial | ½ hour | 1 hour | 2 hours | 24 hours | 24.5 Hours |
| 1026 | Poor | Excellent | Homogenous thick white emulsion | 0.5 ml bottom cream | 0.5 ml bottom cream | 0.5 ml bottom cream | 3.2 ml bottom cream, trace oil | 0.5 ml bottom cream |
| Example 4 | | | | | | | | |
| 20 | Poor | Poor | Homogenous, thick white emulsion | 7 ml top cream | 7 ml top cream | 7 ml top cream | 7 ml top cream, long, fine crystals observed | 5 ml top cream |
| 342 | Poor | Poor | Homogenous, thick white emulsion | 4 ml top cream | 4 ml top cream | 4 ml top cream | 4 ml top oil/cream, long, fine crystals observed | 2 ml top oil/cream |
| 1026 | Poor | Poor | Homogenous, thick white emulsion | 3 ml top cream | 3.8 ml top cream | 4 ml top cream | 4 ml top cream, coarse crystals observed | Nil cream/oil |

It will be clear from the above examples that only Example 1, containing benzyl acetate in combination with the substantially water-miscible co-solvent, was able to overcome the problem of crystallisation upon dilution caused by reliance on the substantially water-miscible co-solvent, while still being sufficiently polar to maintain the solubility of the active ingredient in the concentrate.

| 20 g/L DIFLUFENICAN, 250 gae/L 2,4D 2-ETHYL HEXYL ESTER | |
|---|---|
| Formulation | g/L |
| 2,4-D 2-ethyl hexyl ester | 250 (acid equivalent) |
| Diflufenican | 20 |
| NANSA EVM ® 70/2E | 50 |
| TERMUL ® 5459 | 50 |
| NMP | 150 |
| Solvent | to volume (1 Liter) |

Example 5

In an appropriately sized beaker, 20 g/L of diflufenican and 250 gae/L of 2,4-D2-ethyl hexyl ester was weighed, followed by the addition of 50 g/L NANSA EVM® 70/2E, 50 g/L TERMUL® 5459 and 150 g/L NMP. The formulation was then made to the required volume with benzyl acetate, and stirred over moderate heat (approx. 60° C.) for 15 minutes until homogenous.

Example 6

As for Example 5, the formulation was made to the required volume with Solvesso® 150, and stirred over moderate heat (approx. 60° C.) for 15 minutes until homogenous.

| Storage Stability Results | | |
|---|---|---|
| Appearance | Example 5 | Example 6 |
| Initial | Clear, homogenous solution | Clear, homogenous solution |
| Post storage, seeded at 0° C. for 7 days | Clear solution with slight crystal growth. Crystals soluble on thawing | Clear solution with slight crystal growth. Crystals soluble on thawing |
| Post storage at 54° C. for 2 weeks | Clear, homogenous solution | Clear, homogenous solution |

| Water Hardness (ppm) | Bloom | Ease of Dispersion in water | Volume (ml) creaming/oil with elapsed time | | | | | |
|---|---|---|---|---|---|---|---|---|
| | | | Initial | ½ hour | 1 hour | 2 hours | 24 hours | 24.5 hours |
| Example 5 | | | | | | | | |
| 20 | Excellent | Excellent | Homogenous, thick white emulsion | Nil cream/oil | Nil cream/oil | Nil cream/oil | 0.3 ml bottom cream, trace crystals observed | Nil cream/oil |
| 342 | Excellent | Excellent | Homogenous, thick white emulsion | Nil cream/oil | Nil cream/oil | Nil cream/oil | 0.1 ml bottom cream, trace crystals observed | 0.1 ml bottom cream |
| 1026 | Excellent | Excellent | Homogenous, thick white emulsion | Nil cream/oil | Nil cream/oil | Nil cream/oil | 0.4 ml bottom cream, trace crystals observed | 0.1 ml bottom cream |

-continued

Emulsion Stability Results

| Water Hardness (ppm) | Bloom | Ease of Dispersion in water | Volume (ml) creaming/oil with elapsed time | | | | | |
|---|---|---|---|---|---|---|---|---|
| | | | Initial | ½ hour | 1 hour | 2 hours | 24 hours | 24.5 hours |
| Example 6 | | | | | | | | |
| 20 | Excellent | Excellent | Homogenous, thick white emulsion | Nil cream/oil | Nil cream/oil | Nil cream/oil | 0.2 ml bottom cream, trace crystals observed | Nil cream/oil |
| 342 | Excellent | Excellent | Homogenous, thick white emulsion | Nil cream/oil | Nil cream/oil | Nil cream/oil | 0.1 ml bottom cream, trace crystals observed | Nil cream/oil |
| 1026 | Excellent | Excellent | Homogenous, thick white emulsion | Nil cream/oil | Nil cream/oil | Nil cream/oil | 0.3 ml bottom cream, trace crystals observed | 0.1 ml bottom cream |

| Water Hardness (ppm) | % w/w diflufenican precipitate recovered following 24.5 hour dilution in water | |
|---|---|---|
| | Example 5 | Example 6 |
| 20 | 2.2 | 2.8 |
| 342 | 1.2 | 5.0 |
| 1026 | 0.5 | 4.6 |
| Average | 1.3 | 4.1 |

It will be clear from the above Examples that Examples 5 and 6, although stable after storage at 0° C. for 7 days, both show trace crystallisation upon dilution in water to form the emulsion after 24 hours. It is evidenced however that Example 5, comprising benzyl acetate in combination with a substantially water miscible co-solvent, shows a 67.5% decrease in the average level of precipitate when compared to Example 6.

| 20 g/L DIFLUFENICAN, 360 gae/L MCPA 2-ETHYL HEXYL ESTER | |
|---|---|
| Formulation | g/L |
| MCPA 2-Ethyl Hexyl Ester | 360 (acid equivalent) |
| Diflufenican | 20 |
| NANSA EVM ® 70/2E | 50 |
| TERMUL ® 5459 | 50 |
| NMP | 150 |
| Solvent | to volume (1 Liter) |

Example 7

In an appropriately sized beaker, 20 g/L of diflufenican and 360 gae/L of MCPA 2-Ethyl Hexyl Ester was weighed, followed by the addition of 50 g/L NANSA EVM® 70/2E, 50 g/L TERMUL® 5459 and 150 g/L NMP. The formulation was then made to the required volume with benzyl acetate, and stirred over moderate heat (approx. 60° C.) for 15 minutes until homogenous.

Example 8

As for Example 7, the formulation was made up to the required volume with Solvesso® 150, and stirred over moderate heat (approx. 60° C.) for 15 minutes until homogenous.

| Storage Stability Results | | |
|---|---|---|
| Appearance | Example 7 | Example 8 |
| Initial | Clear, homogenous solution | Clear, homogenous solution |
| Post storage, seeded at 0° C. for 7 days | Clear solution with slight crystal growth. Crystals recoverable on thawing | Clear solution with slight crystal growth. Crystals recoverable on thawing |
| Post storage at 54° C. for 2 weeks | Clear, homogenous solution | Clear, homogenous solution |

Emulsion Stability Results

| Water Hardness (ppm) | Bloom | Ease of Dispersion in water | Volume (ml) creaming/oil with elapsed time | | | | | |
|---|---|---|---|---|---|---|---|---|
| | | | Initial | ½ hour | 1 hour | 2 hours | 24 hours | 24.5 hours |
| Example 7 | | | | | | | | |
| 20 | Excellent | Excellent | Homogenous, thick white emulsion | Nil cream/oil | Nil cream/oil | Nil cream/oil | 0.2 ml bottom cream, trace crystals observed | 0.1 ml bottom cream |
| 342 | Excellent | Excellent | Homogenous, thick white emulsion | Nil cream/oil | Nil cream/oil | Nil cream/oil | 0.2 ml bottom cream, trace crystals observed | Nil cream/oil |

-continued

| Water Hardness (ppm) | Ease of Dispersion in water | | Volume (ml) creaming/oil with elapsed time | | | | | |
|---|---|---|---|---|---|---|---|---|
| | Bloom | sion in water | Initial | ½ hour | 1 hour | 2 hours | 24 hours | 24.5 hours |
| 1026 | Excellent | Excellent | Homogenous, thick white emulsion | Nil cream/oil | Nil cream/oil | Nil cream/oil | 0.2 ml bottom cream, trace crystals observed | Nil cream/oil |

Emulsion Stability Results

Example 8

| 20 | Excellent | Excellent | Homogenous, thick white emulsion | Nil cream/oil | Nil cream/oil | Nil cream/oil | 0.4 ml bottom cream, trace crystals 2.8% | 0.1 ml bottom cream |
| 342 | Excellent | Excellent | Homogenous, thick white emulsion | Nil cream/oil | Nil cream/oil | Nil cream/oil | 0.2 ml bottom cream fine crystals, 5.9% | Nil cream/oil |
| 1026 | Excellent | Excellent | Homogenous, thick white emulsion | Nil cream/oil | Nil cream/oil | Nil cream/oil | 0.2 ml bottom cream Fine crystals, 5.7% | Nil cream/oil |

| Water Hardness (ppm) | % w/w diflufenican precipitate recovered following 24.5 hour dilution in water | |
|---|---|---|
| | Example 7 | Example 8 |
| 20 | 4.3 | 2.8 |
| 342 | 3.2 | 5.9 |
| 1026 | 3.2 | 5.7 |
| Average | 3.6 | 4.8 |

It will be clear from the above Examples that Examples 7 and 8, although stable after storage at 0° C. for 7 days, both show trace crystallisation upon dilution in water to form the emulsion after 24 hours. It is evidenced however that Example 7, comprising benzyl acetate in combination with a substantially water miscible co-solvent, shows a 25.7% decrease in the average level of precipitate when compared to Example 8.

360 g/L PROPANIL

| Formulation | g/L |
|---|---|
| Propanil | 360 |
| Isophorone | 170 |
| TERIC ® 217 | 160 |
| Solvent | To volume (1 Liter) |

Example 9

In an appropriately sized beaker, 360 g/L of propanil was weighed, followed by the addition of 170 g/L of isophorone and 160 g/L of TERIC® 217. The formulation was then made to volume with benzyl acetate, and stirred over moderate heat (approx. 60° C.) for 15 minutes until homogenous.

Example 10 (Comparative Example)

As for Example 5, the formulation was made to volume with xylene, and stirred over moderate heat (approx. 60° C.) for 15 minutes until homogenous.

Storage Stability Results

| Appearance | Example 9 | Example 10 |
|---|---|---|
| Initial | Clear, yellow, homogenous solution | Clear, yellow, homogenous solution |
| Post-storage, seeded at 0° C. for 7 days | Clear, yellow solution with crystal growth. Crystals soluble on thawing | Clear, yellow solution with crystal growth. Crystals insoluble on thawing |
| Post-storage at 54° C. for 2 weeks | Clear, yellow, homogenous solution | Clear, yellow, homogenous solution |

Emulsion Stability Results

| Water Hardness (ppm) | Ease of Dispersion in water | | Volume (ml) creaming/oil with elapsed time | | | | | |
|---|---|---|---|---|---|---|---|---|
| | Bloom | sion in water | Initial | ½ hour | 1 hour | 2 hours | 24 hours | 24.5 hours |

Example 9

| 20 | Poor | Good | Homogenous thin cream emulsion | 4.9 ml bottom cream/ trace oil | 4.9 ml bottom cream/ trace oil | 4.9 ml bottom cream/oil | 4.9 ml bottom cream/oil, no crystals observed | 5.0 ml bottom cream |
| 342 | Poor | Good | Homogenous thin cream emulsion | 4.0 ml bottom cream | 4.3 ml bottom cream | 4.5 ml bottom cream | 4.3 ml bottom cream/oil, no crystals observed | 2.1 ml bottom cream |

| Emulsion Stability Results | | | | | | | | |
|---|---|---|---|---|---|---|---|---|
| Water Hardness | | Ease of Dispersion in water | Volume (ml) creaming/oil with elapsed time | | | | | |
| (ppm) | Bloom | | Initial | ½ hour | 1 hour | 2 hours | 24 hours | 24.5 hours |
| 1026 | Poor | Good | Homogenous thin cream emulsion | 4.1 ml bottom cream | 4.2 ml bottom oil | 4.2 ml bottom oil | 4.5 ml bottom oil, no crystals observed | 4.0 ml bottom oil |
| Example 10 | | | | | | | | |
| 20 | Good | Excellent | Homogenous thick cream emulsion | 0.2 ml bottom cream | 0.2 ml bottom cream | 0.2 ml bottom cream | 3.1 ml bottom cream, coarse crystals observed | 0.2 ml bottom cream |
| 342 | Good | Excellent | Homogenous thick cream emulsion | 0.4 ml bottom cream | 0.6 ml bottom cream | 0.7 ml bottom cream | 1.1 ml bottom cream, trace fine crystals observed | 0.1 ml bottom cream |
| 1026 | Good | Excellent | Homogenous thick cream emulsion | 0.6 ml bottom cream | 0.9 ml bottom cream/oil | 0.9 ml bottom cream/oil | 1.4 ml bottom cream/oil, coarse crystals observed | 1.1 ml bottom oil |

It will be clear from the above Examples that only Example 9, containing benzyl acetate in combination with the substantially water-miscible co-solvent, was able to overcome the problem of crystallisation upon dilution caused by reliance on the substantially water-miscible co-solvent, while still being sufficiently polar to maintain the solubility of the active in the concentrate.

| 240 g/L OXYFLUORFEN | |
|---|---|
| Formulation | g/L |
| Oxyfluorfen | 240 |
| TERIC ® 200 | 33 |
| TERIC ® 16M15 | 14 |
| NANSA ® EVM 70/2E | 58.5 |
| Solvent | To volume (1 Liter) |

Example 11 (Comparative Example)

In an appropriately sized beaker, 240 g/L of oxyfluorfen was weighed, followed by the addition of 33 g/L of TERIC® 200, 14 g/L of TERIC® 16M15 and 58.5 g/L NANSA® EVM 70/2E. The formulation was then made to volume with benzyl acetate, and stirred over moderate heat (approx. 60° C.) for 15 minutes until homogenous.

Example 12 (Comparative Example)

As for Example 11, 150 g/L NMP was added and made up to volume with Solvesso® 150, and then stirred over moderate heat (approx. 60° C.) for 15 minutes until homogenous.

Example 13

As for Example 11, 150 g/L NMP was added and made to volume with benzyl acetate, and then stirred over moderate heat (approx. 60° C.) for 15 minutes until homogenous.

| Storage Stability Results | | | |
|---|---|---|---|
| Appearance | Example 11 | Example 12 | Example 13 |
| Initial | Clear, red, homogenous solution | Clear, red, homogenous solution | Clear, red, homogenous solution |
| Post-storage, seeded at 0° C. for 7 days | Hazy solution with crystal growth. Crystals insoluble on thawing | Clear solution with crystal growth. Crystals soluble on thawing. | Clear solution with crystal growth. Crystals soluble on thawing. |
| Post-storage at 54° C. for 2 weeks | Clear, red, homogenous solution | Clear, red, homogenous solution | Clear, red, homogenous solution |

| Emulsion Stability Results | | | | | | | | |
|---|---|---|---|---|---|---|---|---|
| Water Hardness | | Ease of Dispersion in water | Volume (ml) creaming/oil with elapsed time | | | | | |
| (ppm) | Bloom | | Initial | ½ hour | 1 hour | 2 hours | 24 hours | 24.5 hours |
| Example 11 | | | | | | | | |
| 20 | Poor | Excellent | Homogenous, thick white emulsion | 6 ml bottom cream | 8 ml bottom cream | 8.1 ml bottom cream | 8.5 ml bottom cream, coarse crystals observed | 6 ml bottom cream |

-continued

| | | | Emulsion Stability Results | | | | | |
|---|---|---|---|---|---|---|---|---|
| Water Hardness | | Ease of Dispersion in water | | Volume (ml) creaming/oil with elapsed time | | | | |
| (ppm) | Bloom | | Initial | ½ hour | 1 hour | 2 hours | 24 hours | 24.5 hours |
| 342 | Poor | Excellent | Homogenous, thick white emulsion | 3 ml bottom cream | 4.5 ml bottom cream | 5.4 ml bottom cream | 7.9 ml bottom cream, coarse crystals observed | 3 ml bottom cream |
| 1026 | Poor | Excellent | Homogenous, thick white emulsion | 2.2 ml bottom cream | 4 ml bottom cream | 5 ml bottom cream | 8 ml bottom cream, coarse crystals observed | 3 ml bottom cream |
| | | | Example 12 | | | | | |
| 20 | Excellent | Excellent | Homogenous, thick pale pink emulsion | Nil cream/oil | Nil cream/oil | Nil cream/oil | Nil cream/oil, coarse crystals observed | Nil cream/oil |
| 342 | Excellent | Excellent | Homogenous, thick pale pink emulsion | Nil cream/oil | Nil cream/oil | Nil cream/oil | Nil cream/oil, coarse crystals observed | Nil cream/oil |
| 1026 | Excellent | Excellent | Homogenous, thick pale pink emulsion | Nil cream/oil | Nil cream/oil | Nil cream/oil | 0.3 ml bottom oil/cream, large coarse crystals observed | 0.3 ml bottom cream/oil |
| | | | Example 13 | | | | | |
| 20 | Poor | Excellent | Homogenous, thick pale pink emulsion | 0.5 ml bottom cream | 0.8 ml bottom cream | 0.8 ml bottom cream | 8.1 ml bottom cream, no crystals observed | trace bottom cream |
| 342 | Poor | Excellent | Homogenous, thick pale pink emulsion | 1.0 ml bottom cream | 1.1 ml bottom cream | 1.8 ml bottom cream | 4.7 ml bottom cream, no crystals observed | 0.8 ml bottom cream |
| 1026 | Poor | Excellent | Homogenous, thick pale pink emulsion | 0.7 ml bottom cream | 0.8 ml bottom cream | 1.2 ml bottom cream | 4.1 ml bottom cream, no crystals observed | 0.5 ml bottom cream |

It will be clear from the above examples that at least 150 g/L of NMP is required to give sufficient solubility of oxyfluorfen in the concentrate. Only Example 11, containing benzyl acetate in combination with the substantially water-miscible co-solvent, was able to overcome the problem of crystallisation on dilution caused by reliance on the substantially water-miscible co-solvent, while still being sufficiently polar to maintain the solubility of the active in the concentrate.

| 100 g/L IMIDACLOPRID (Imidacloprid is insoluble in benzyl acetate) | |
|---|---|
| Formulation | g/L |
| Imidacloprid | 100 |
| TERMUL ® 200 | 50 |
| NANSA ® EVM70/2E | 50 |
| NMP | 417 |
| Solvent | To volume (1 Liter) |

Example 14

In an appropriately sized beaker, 100 g/L of imidacloprid was weighed, followed by the addition of 417 g/L of NMP, 50 g/L TERMUL® 200, and 50 g/L NANSA® EVM70/2E. The formulation was then made to volume with benzyl acetate, and stirred over moderate heat (approx. 60° C.) for 15 minutes until homogenous.

Example 15

As for Example 14, the formulation was made to volume with a 10:90 blend of DMSO/benzyl acetate, and stirred over moderate heat (approx. 60° C.) for 15 minutes until homogenous.

| | Storage Stability Results | |
|---|---|---|
| Appearance | Example 14 | Example 15 |
| Initial | Clear, homogenous solution | Clear, homogenous solution |
| Post-storage, seeded at 0° C. for 7 days | Clear solution with crystal growth. Crystals insoluble on thawing | Clear solution with no crystal growth |
| Post-storage at 54° C. for 2 weeks | Clear, homogenous solution | Clear, homogenous solution |

Emulsion Stability Results

| Water Hardness (ppm) | Bloom | Ease of Dispersion in water | Initial | ½ hour | 1 hour | 2 hours | 24 hours | 24.5 hours |
|---|---|---|---|---|---|---|---|---|
| | | | | | | | | |
| Example 14 ||||||||||
| 20 | Excellent | Excellent | Homogenous, thin white emulsion | Long fine crystals observed, nil cream/oil | Long fine crystals observed, nil cream/oil | Long fine crystals observed, nil cream/oil | nil cream/oil, coarse crystals observed | 15 ml bottom crystals observed |
| 342 | Excellent | Excellent | Homogenous, thin white emulsion | Long fine crystals observed, nil cream/oil | Long fine crystals observed, nil cream/oil | Long fine crystals observed, nil cream/oil | nil cream/oil, coarse crystals observed | 18 ml bottom crystals observed |
| 1026 | Excellent | Excellent | Homogenous, thin white emulsion | Long fine crystals observed, Nil cream/oil | Long fine crystals observed, nil cream/oil | Long fine crystals observed, nil cream/oil | 45 ml of crystals, top thinning, coarse crystals observed | 21 ml bottom crystals observed |
| Example 15 ||||||||||
| 20 | Excellent | Excellent | Homogenous, thick white emulsion | Nil cream/oil | Nil cream/oil | 0.1 ml bottom cream | 0.5 ml bottom cream, coarse crystals observed | Bottom crystals observed |
| 342 | Excellent | Excellent | Homogenous, thick white emulsion | Nil cream/oil | Nil cream/oil | Nil cream/oil | Nil cream/oil, coarse crystals observed | Bottom crystals observed |
| 1026 | Excellent | Excellent | Homogenous, thick white emulsion | Nil cream/oil | Nil cream/oil, top thinning | 28ml bottom cream, top thinning | 65 ml bottom crystals/cream, coarse crystals observed | Bottom crystals observed |

It can be seen from the above Examples that, while none of the formulations completely prevent crystallisation of the diluted emulsion after 24 hours, the embodiment example shows a great improvement and delay in the crystallisation. Therefore Example 15 is potentially a useable formulation.

250 g/L BIFENTHRIN

| Formulation | g/L |
|---|---|
| Bifenthrin | 250 |
| TERMUL ® 3150 | 150 |
| TERIC ® 13A9 | 100 |
| Solvent | To volume (1 Liter) |

Example 16 (Comparative Example)

In an appropriately sized beaker, 250 g/L of melted bifenthrin was weighed, followed by 150 g/L of TERMUL 3150®, 100 g/L of TERIC® 13A9. The formulations was then made to the required volume with an 80:20 blend of benzyl acetate/Solvesso® 150, and stirred over moderate heat (approx. 60° C.) for 15 minutes until homogenous.

Example 17

As for Example 16, 50 g/L of DMSO was added and the formulation was made to the required volume with benzyl acetate, then stirred over moderate heat (approx. 60° C.) for 15 minutes until homogenous.

Example 18 (Comparative Example)

As for Example 16, 250 g/L JEFFSOL® AG 1710 was added and the formulation was made to the required volume with benzyl acetate, and stirred over moderate heat (approx. 60° C.) for 15 minutes until homogenous. JEFFSOL® AG 1710 is a dibasic ester solvent which is not substantially water miscible.

Storage Stability Results

| Appearance | Example 16 | Example 17 | Example 18 |
|---|---|---|---|
| Initial | Clear, homogenous solution | Clear, homogenous solution | Clear, homogenous solution |
| Post-storage, seeded at 0° C. for 7 days | Clear solution with crystal growth. Crystals insoluble on thawing | Clear solution with no crystal growth | Clear solution with crystal growth. Crystals soluble on thawing |
| Post-storage at 54° C. for 2 weeks | Clear, homogenous solution | Clear, homogenous solution | Clear, homogenous solution |

| Water Hardness (ppm) | Bloom | Ease of Dispersion in water | Initial | Volume (ml) creaming/oil with elapsed time | | | | |
|---|---|---|---|---|---|---|---|---|
| | | | | ½ hour | 1 hour | 2 hours | 24 hours | 24.5 Hours |
| Example 16 | | | | | | | | |
| 20 | Excellent | Excellent | Homogenous, thick white emulsion | Nil cream/oil | Nil cream/oil | Nil cream/oil | Nil cream/oil, no crystals observed | Nil cream/oil |
| 342 | Excellent | Excellent | Homogenous, thick white emulsion | Nil cream/oil | Nil cream/oil | Nil cream/oil | Nil cream/oil, no crystals observed | Nil cream/oil |
| 1026 | Excellent | Excellent | Homogenous, thick white emulsion | 0.1 ml bottom cream | 0.1 ml bottom cream | 0.1 ml bottom cream | 0.3 ml bottom cream, no crystals observed | Nil cream/oil |
| Example 17 | | | | | | | | |
| 20 | Excellent | Excellent | Homogenous, thick white emulsion | Nil cream/oil | Nil cream/oil | Nil cream/oil | Nil cream, trace oil, no crystals observed | Nil cream/oil |
| 342 | Excellent | Excellent | Homogenous, thick white emulsion | Nil cream/oil | Nil cream/oil | Nil cream/oil | Nil cream/oil, no crystals observed | Nil cream/oil |
| 1026 | Excellent | Excellent | Homogenous, thick white emulsion | Nil cream/oil | Nil cream/oil | Nil cream/oil | Nil cream/oil, no crystals observed | Nil cream/oil |
| Example 18 | | | | | | | | |
| 20 | Excellent | Excellent | Homogenous, thick white emulsion | Nil cream/oil | Nil cream/oil | Nil cream/oil | Nil cream/oil, crystals observed | Nil cream/oil |
| 342 | Excellent | Excellent | Homogenous, thick white emulsion | Nil cream/oil | Nil cream/oil | Nil cream/oil | Nil cream/oil, crystals observed | Nil cream/oil |
| 1026 | Excellent | Excellent | Homogenous, thick white emulsion | Nil cream/oil | Nil cream/oil | Nil cream/oil | Nil cream/oil, coarse crystals observed | Nil cream/oil |

It will be clear from these examples that only Example 17, containing benzyl acetate in combination with the substantially water-miscible co-solvent, was able to overcome the problem of crystallisation upon dilution caused by reliance on the substantially water-miscible co-solvent, while still being sufficiently polar to maintain the solubility of the active ingredient in the concentrate.

The very high volumes of cream referred to in some results are from a "setting-up" of crystals and emulsion phase to form a separate visible phase and so do not reflect directly the mass of crystals or the true volume of cream.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

Where the terms "comprise", "comprises", "comprised" or "comprising" or the terms "include", "includes", "included" or "including" are used in this specification, they are to be interpreted as specifying the presence of the stated features, integers, steps or components referred to, but not to preclude the presence or addition of one or more other feature, integer, step, component or group thereof.

Further, any prior art reference or statement provided in the specification is not to be taken as an admission that such art constitutes, or is to be understood as constituting, part of the common general knowledge.

The invention claimed is:

1. An agrochemical emulsifiable concentrate (EC) formulation comprising at least one agrochemical active ingredient, at least one surfactant emulsifier, a primary solvent system, and optionally a stabilizer wherein the primary solvent system is a mixture of benzyl acetate and a sufficient amount of at least one polar substantially water-miscible co-solvent selected from the group consisting of N-methylpyrrolidinone (NMP), dimethylsulphoxide (DMSO), dimethylisosorbide (DMI), ethylene carbonate, propylene carbonate, butylene carbonate, dimethylcarbonate, diethylcarbonate, an alkyl glycol ether and mixtures thereof and wherein the weight ratio of benzyl acetate to the polar, substantially water-miscible co-solvent is in the range of from 90:10 to 60:40.

2. A formulation according to claim 1, wherein the active ingredient is present in a concentration, which is partially soluble in the benzyl acetate and the water-miscible co-solvent after storage at 0° C. with crystal seeding.

3. A formulation according to claim 1, wherein the active ingredient is selected from the group consisting of pyridine-based herbicides, diphenylether herbicides, anilide herbicides, dinitroaniline herbicides, triazole fungicides, carbamate insecticides, oxadiazine insecticides, synthetic pyrethroid insecticides, neonicotinoid insecticides and mixtures thereof.

4. A formulation according to claim 3, wherein the active ingredient is selected from the group consisting of clopyralid, diflufenican, oxyfluorfen, propanil, triadimenol, oryzalin, propoxur, bifenthrin, indoxacarb, imidacloprid, thiacloprid and mixtures thereof.

5. A formulation according to claim 4, wherein the active ingredient is diflufenican present at greater than 2% weight/volume.

6. A formulation according to claim 5, further comprising a phenoxyacid ester herbicide.

7. A formulation according to claim 1, further comprising one or more water-immiscible non-primary co-solvent(s), wherein the water-immiscible co-solvent is not required to dissolve the active ingredient.

8. A formulation according to claim 1, wherein the surfactant emulsifier(s) is selected from the group consisting of alkoxylated alcohols, alkoxylated alkylphenols, ethoxylated fatty acids, ethoxylated vegetable oils, ethoxylated tristyrylphenol, fatty acid esters of sorbitol and ethoxylated derivatives thereof, ethoxylated amines and condensates of glycerol, sulfonated alkylbenzenes in the range $C_{11}$-$C_{16}$ and salts thereof, alkylether sulphates, alkyletherphosphates, alkylphenoletherphosphates, a catanionic system, wherein a cationic amine is used in combination with one or more alkylsulphonate(s), ether sulphate(s) or alkyletherphosphate(s) and combinations thereof.

9. A formulation according to claim 8, wherein the stabilizer is selected from the group consisting of butylated hydroxytoluene (BHT) and epoxidized soybean oil (ESBO).

10. A formulation according to claim 9, wherein the stabilizer is present in a concentration of up to 3% weight/volume.

11. An emulsion-in-water (EW) formulation, wherein an EC formulation according to claim 1 is further diluted in water to form a concentrated agrochemical formulation.

12. A method of making an EW formulation according to claim 11, wherein the method comprises the following steps:
(a) forming a mixture comprising the agrochemical active ingredient, the polar, substantially water-miscible co-solvent, and benzyl acetate;
(b) adding the surfactant emulsifier and optionally the stabilizer to form the EC formulation; and
(c) contacting said EC formulation obtained in step (b) with water to form the EW formulation.

13. A method according to claim 12, wherein step (a) comprises:
a) forming a mixture of the agrochemical active ingredient in benzyl acetate and then adding the polar, substantially water-miscible co-solvent; or
b) forming a mixture of the agrochemical active ingredient in the polar, substantially water-miscible co-solvent and then adding benzyl acetate; or
c) forming a mixture of the agrochemical active ingredient in a combination of benzyl acetate and the polar, substantially water-miscible co-solvent; or
d) combining the agrochemical active ingredient, benzyl acetate and the polar, substantially water-miscible co-solvent.

14. A method of making an EC formulation comprising at least one agrochemical active ingredient, wherein the method comprises the following steps:
(a) forming a mixture comprising the agrochemical active ingredient, a polar, substantially water-miscible co-solvent selected from the group consisting of N-methylpyrrolidinone (NMP), dimethylsulphoxide (DMSO), dimethylisosorbide (DMI), ethylene carbonate, propylene carbonate, butylene carbonate, dimethylcarbonate, diethylcarbonate, an alkyl glycol ether and mixtures thereof, and benzyl acetate and wherein the weight ratio of benzyl acetate to the polar, substantially water-miscible co-solvent is in the range of from 90:10 to 60:40; and
(b) adding a suitable surfactant emulsifier and optionally a stabilizer.

15. A method of making an EC formulation according to claim 14, wherein step (a) comprises:
a) forming a mixture of the agrochemical active ingredient in benzyl acetate and then adding the polar, substantially water-miscible co-solvent; or
b) forming a mixture of the agrochemical active ingredient in the polar, substantially water-miscible co-solvent and then adding benzyl acetate; or
c) forming a mixture of the agrochemical active ingredient in a combination of benzyl acetate and the polar, substantially water-miscible co-solvent; or
d) combining the agrochemical active ingredient, benzyl acetate and the polar, substantially water-miscible co-solvent.

* * * * *